US008920457B2

(12) United States Patent
Davis, III et al.

(10) Patent No.: US 8,920,457 B2
(45) Date of Patent: *Dec. 30, 2014

(54) MODIFIED HEADPIECE FOR HYDRAULIC COIL DEPLOYMENT SYSTEM

(75) Inventors: Richard Champion Davis, III, Plantation, FL (US); Amanda E. Jordan, Pembroke Pines, FL (US)

(73) Assignee: Depuy Synthes Products LLC, Raynham, MA (US)

(*) Notice: Subject to any disclaimer, the term of this patent is extended or adjusted under 35 U.S.C. 154(b) by 513 days.

This patent is subject to a terminal disclaimer.

(21) Appl. No.: 12/821,863

(22) Filed: Jun. 23, 2010

(65) Prior Publication Data

US 2010/0262179 A1  Oct. 14, 2010

Related U.S. Application Data

(60) Division of application No. 11/560,958, filed on Nov. 17, 2006, now Pat. No. 7,766,935, which is a continuation-in-part of application No. 11/423,525, filed on Jun. 12, 2006, now Pat. No. 7,670,353.

(51) Int. Cl.
  *A61M 29/00* (2006.01)
  *A61B 17/12* (2006.01)
  *A61B 17/00* (2006.01)

(52) U.S. Cl.
  CPC ....... *A61B 17/12022* (2013.01); *A61B 17/1214* (2013.01); *A61B 17/1219* (2013.01); *A61B 2017/00539* (2013.01); *A61B 2017/12054* (2013.01); *A61B 2017/1205* (2013.01)
  USPC ........................................................ 606/200

(58) Field of Classification Search
  USPC ................ 606/200, 192, 191, 108; 623/23.72
  See application file for complete search history.

(56) References Cited

U.S. PATENT DOCUMENTS

| 4,390,599 | A | 6/1983 | Broyles |
| 4,864,824 | A | 9/1989 | Gabriel et al. |
| 4,981,756 | A | 1/1991 | Rhandhawa |
| 5,061,914 | A | 10/1991 | Busch et al. |
| 5,082,359 | A | 1/1992 | Kirkpatrick |
| 5,167,624 | A | 12/1992 | Butler et al. |
| 5,178,957 | A | 1/1993 | Kolpe et al. |
| 5,197,978 | A | 3/1993 | Hess |
| 5,288,230 | A | 2/1994 | Nikutowski et al. |
| 5,334,216 | A | 8/1994 | Vidal et al. |
| 5,360,397 | A | 11/1994 | Pinchuk |
| 5,403,700 | A | 4/1995 | Heller et al. |
| 5,543,019 | A | 8/1996 | Lee et al. |
| 5,607,463 | A | 3/1997 | Schwartz et al. |
| 5,629,077 | A | 5/1997 | Turnlund et al. |
| 5,656,036 | A | 8/1997 | Palmaz |
| 5,669,931 | A | 9/1997 | Kupiecki et al. |
| 5,669,977 | A | 9/1997 | Shufflebotham et al. |
| 5,681,575 | A | 10/1997 | Burrell et al. |
| 5,685,961 | A | 11/1997 | Pourrezaei et al. |

(Continued)

*Primary Examiner* — Gregory Anderson
*Assistant Examiner* — Christina Lauer
(74) *Attorney, Agent, or Firm* — Cook Alex Ltd.

(57) ABSTRACT

A vascular occlusion device for use with a hydraulic deployment catheter is provided. The vascular occlusion device includes a headpiece that has a deformable interference element which changes from an initial configuration to a deformed configuration upon an increase of hydraulic pressure within the deployment catheter. When the interference element is in the initial configuration, the headpiece is secured to the deployment catheter, and when the interference element is in the deformed configuration, the headpiece can be removed from the deployment catheter for deployment of the occlusion device.

15 Claims, 4 Drawing Sheets

(56) References Cited

U.S. PATENT DOCUMENTS

| | | |
|---|---|---|
| 5,735,892 A | 4/1998 | Myers et al. |
| 5,744,958 A | 4/1998 | Werne |
| 5,753,251 A | 5/1998 | Burrell et al. |
| 5,766,710 A | 6/1998 | Turnlund et al. |
| 5,770,255 A | 6/1998 | Burrell et al. |
| 5,810,870 A | 9/1998 | Myers et al. |
| 5,843,289 A | 12/1998 | Lee et al. |
| 5,902,317 A | 5/1999 | Kleshinski et al. |
| 5,908,409 A | 6/1999 | Rinehart et al. |
| 5,925,038 A | 7/1999 | Panescu et al. |
| 5,925,075 A | 7/1999 | Myers et al. |
| 5,945,153 A | 8/1999 | Dernaley |
| 5,951,586 A | 9/1999 | Bert et al. |
| 5,976,162 A | 11/1999 | Doan et al. |
| 6,013,084 A | 1/2000 | Ken et al. |
| 6,017,553 A | 1/2000 | Burrell et al. |
| 6,043,451 A | 3/2000 | Julien et al. |
| 6,096,175 A | 8/2000 | Roth |
| 6,174,329 B1 | 1/2001 | Callol et al. |
| 6,203,732 B1 | 3/2001 | Clubb et al. |
| 6,238,415 B1 | 5/2001 | Sepetka et al. |
| 6,238,686 B1 | 5/2001 | Burrell et al. |
| 6,319,277 B1 | 11/2001 | Rudnick et al. |
| 6,322,588 B1 | 11/2001 | Ogle et al. |
| 6,325,824 B2 | 12/2001 | Limon |
| 6,342,067 B1 | 1/2002 | Mathis et al. |
| 6,428,557 B1 | 8/2002 | Hilaire |
| 6,432,116 B1 | 8/2002 | Callister et al. |
| 6,436,132 B1 | 8/2002 | Patel et al. |
| 6,447,478 B1 | 9/2002 | Maynard |
| 6,458,119 B1 | 10/2002 | Berenstein et al. |
| 6,471,721 B1 | 10/2002 | Dang |
| 6,527,919 B1 | 3/2003 | Roth |
| 6,533,905 B2 | 3/2003 | Johnson et al. |
| 6,537,310 B1 | 3/2003 | Palmaz et al. |
| 6,544,225 B1 * | 4/2003 | Lulo et al. ............ 604/104 |
| 6,544,255 B2 | 4/2003 | Stewart |
| 6,605,111 B2 | 8/2003 | Bose et al. |
| 6,627,246 B2 | 9/2003 | Mehta et al. |
| 6,645,243 B2 | 11/2003 | Vallana et al. |
| 6,660,032 B2 | 12/2003 | Klumb et al. |
| 6,666,882 B1 | 12/2003 | Bose et al. |
| 6,689,141 B2 * | 2/2004 | Ferrera et al. ............ 606/108 |
| 6,726,993 B2 | 4/2004 | Teer et al. |
| 6,786,920 B2 | 9/2004 | Shannon et al. |
| 6,805,898 B1 | 10/2004 | Wu et al. |
| 6,994,711 B2 | 2/2006 | Hieshima et al. |
| 7,766,935 B2 * | 8/2010 | Davis et al. ............ 606/200 |
| 2001/0020182 A1 | 9/2001 | Klumb et al. |
| 2001/0039449 A1 | 11/2001 | Johnson et al. |
| 2002/0032478 A1 | 3/2002 | Boekstegers et al. |
| 2002/0038143 A1 | 3/2002 | McCrea et al. |
| 2002/0111667 A1 | 8/2002 | Girton et al. |
| 2002/0151958 A1 | 10/2002 | Chuter |
| 2003/0004567 A1 | 1/2003 | Boyle et al. |
| 2003/0066533 A1 | 4/2003 | Loy |
| 2004/0034363 A1 | 2/2004 | Wilson et al. |
| 2004/0098094 A1 | 5/2004 | Boyle et al. |
| 2004/0143288 A1 | 7/2004 | Searle |

* cited by examiner

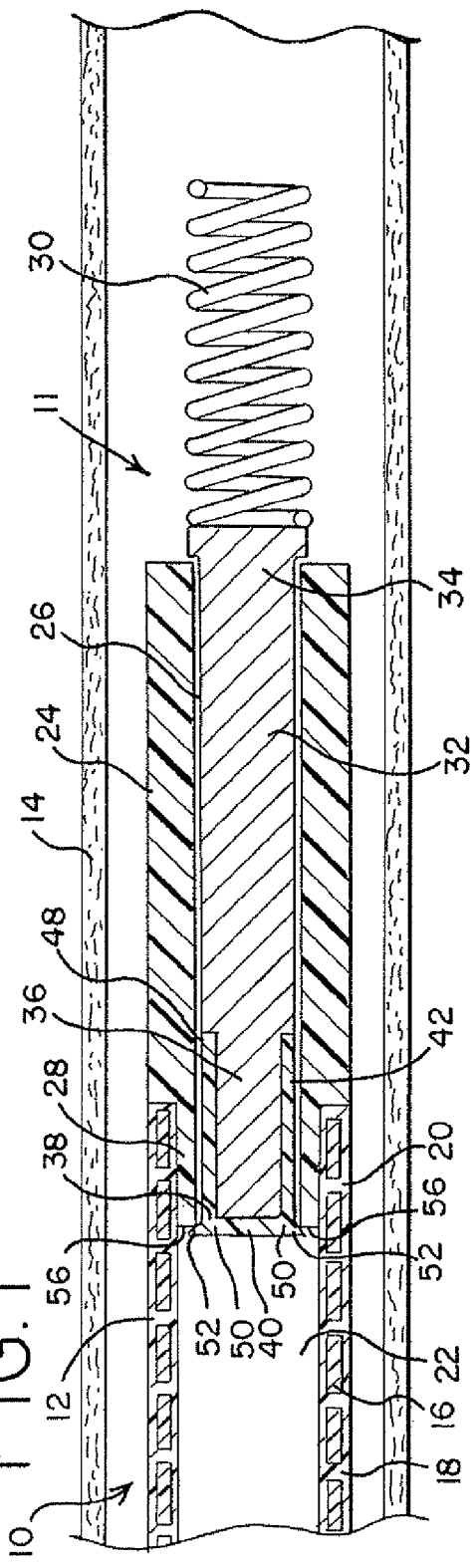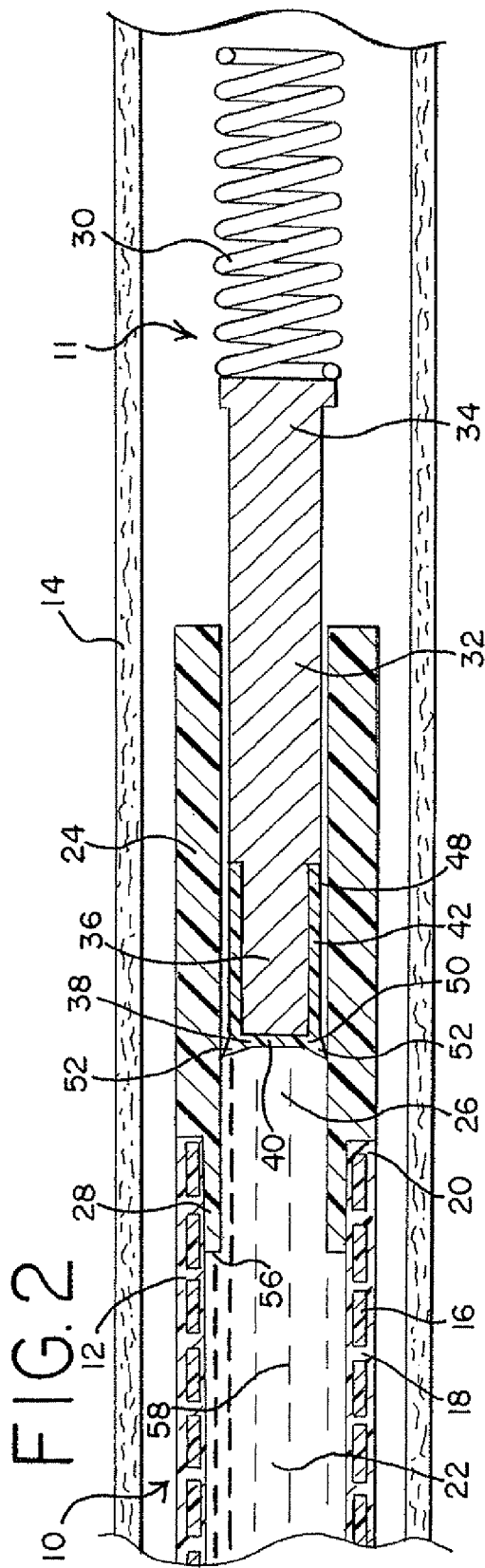

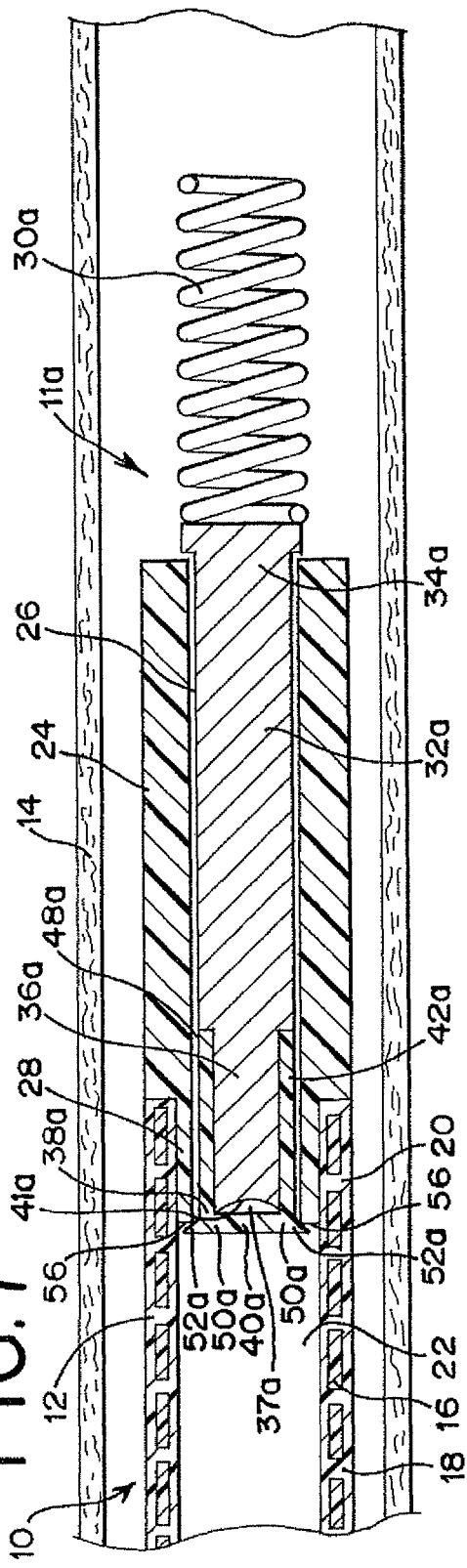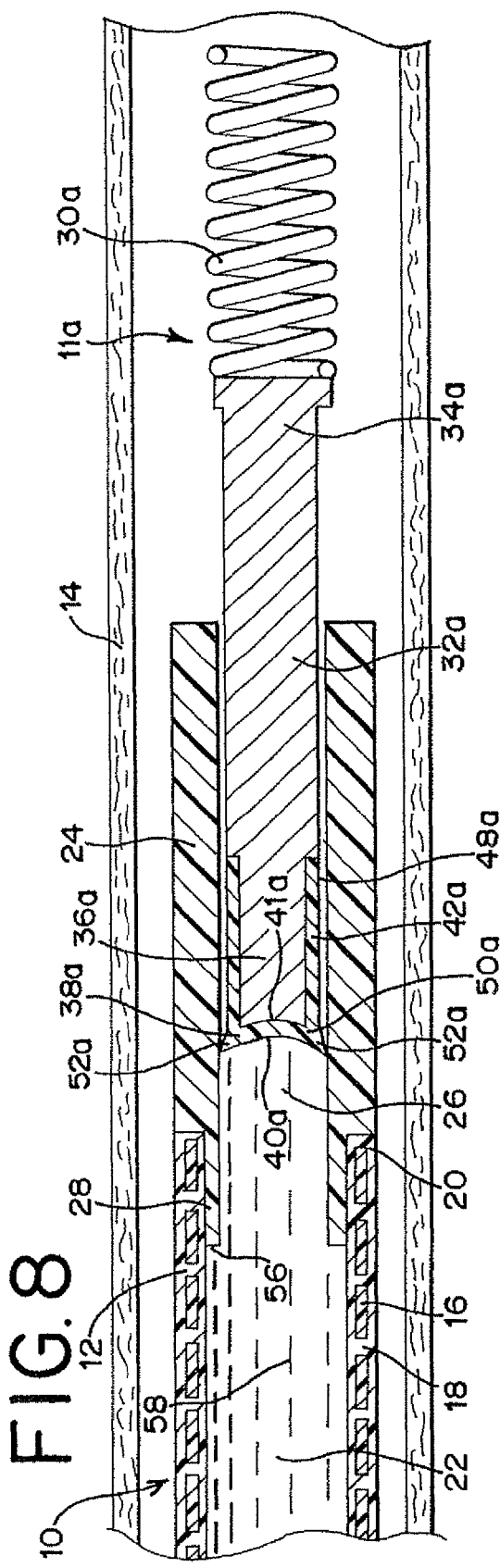

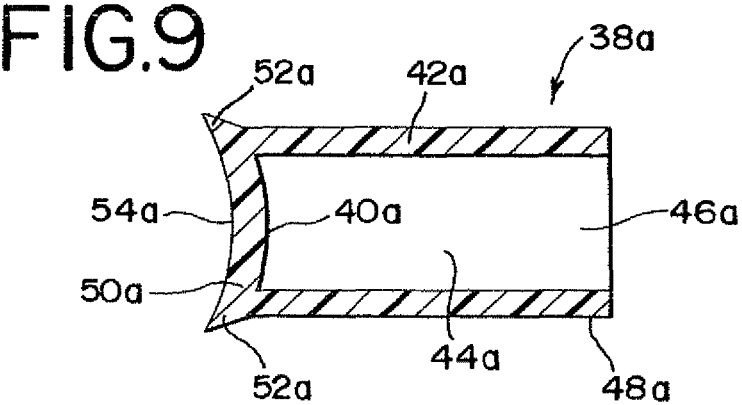
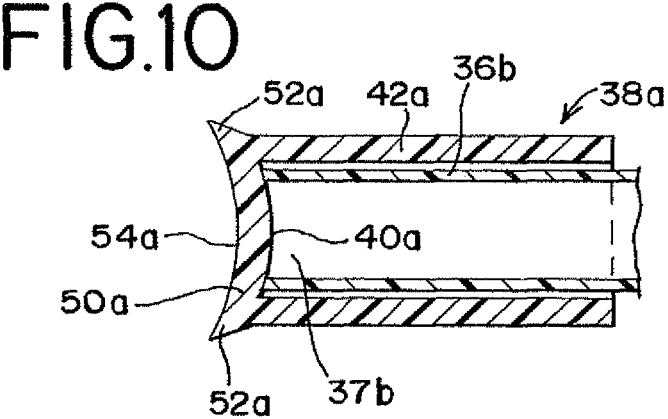

MODIFIED HEADPIECE FOR HYDRAULIC COIL DEPLOYMENT SYSTEM

This application is a divisional of application Ser. No. 11/560,958, now U.S. Pat. No. 7,766,935, filed Nov. 17, 2006, which is a continuation-in-part of U.S. patent application Ser. No. 11/423,525, now U.S. Pat. No. 7,670,353, filed Jun. 12, 2006, both hereby incorporated by reference hereinto.

FIELD OF THE INVENTION

The present invention is related to the delivery of embolic occlusion devices. Disclosed are occlusion devices having a modified headpiece for use with hydraulic deployment systems and methods for deploying such occlusion devices at a preselected location within a patient, in an accurate and rapid manner. The occlusion devices and methods are particularly well suited for deployment of the occlusion devices at a location of concern within the vasculature, especially intracranially, of a patient.

BACKGROUND OF THE INVENTION

The use of catheter delivery systems for positioning and deploying therapeutic devices, such as dilation balloons, stents and embolic coils, in the vasculature of the human body has become a standard procedure for treating endovascular diseases. It has been found that such devices are particularly useful in treating areas where traditional operational procedures are impossible or pose a great risk to the patient, for example in the treatment of aneurysms in intracranial blood vessels. Due to the delicate tissue surrounding intracranial blood vessels, especially for example brain tissue, it is very difficult and often risky to perform surgical procedures to treat defects of intracranial blood vessels. Advancements in catheter deployment systems have provided an alternative treatment in such cases. Some of the advantages of catheter delivery systems are that they provide methods for treating blood vessels by an approach that has been found to reduce the risk of trauma to the surrounding tissue, and they also allow for treatment of blood vessels that in the past would have been considered inoperable.

Typically, these procedures involve inserting the distal end of a guiding catheter into the vasculature of a patient and traversing it through the vasculature to a predetermined delivery site. A vascular occlusion device, such as an embolic coil, is attached to the distal end of a deployment catheter which pushes the occlusion device through the guiding catheter and out of the distal end of the guiding catheter into the delivery site. Some of the problems that have been associated with these procedures relate to the accuracy of occlusion device placement. For example, once the occlusion device is pushed out of the distal end of the guiding catheter, the occlusion device cannot be retracted and may migrate to an undesired location. Often, retrieving and repositioning the occlusion devices requires a separate procedure and has the potential to expose the patient to additional risk.

In response to the above mentioned concerns, numerous devices and release mechanisms have been developed in an attempt to create delivery systems which provide both control of an occlusion device after the device has exited the guiding catheter and a rapid release or detachment mechanism to release the device from the deployment catheter once the occlusion device is in place.

One such device is disclosed in Lulo at al. U.S. Pat. No. 6,544,225, currently assigned to the same assignee as the subject application and hereby incorporated herein by reference. Lulo et al. discloses a hydraulic deployment system that has a deployment catheter having a lumen extending throughout the length of the catheter. The catheter has a distal end portion that is formed from a material which expands outwardly when a liquid is applied within the lumen of the catheter. A proximal end portion of an occlusion device is disposed in fluid-tight engagement within the lumen of the distal portion of the catheter. The proximal end portion of the occlusion device is typically a generally cylindrical section that, prior to assembly of the system, has a greater diameter than the distal end portion of the deployment catheter prior to assembly of the system and prior to expansion. A frictional engagement is formed by inserting the larger diameter proximal end portion of the occlusion device into the smaller diameter distal end portion of the deployment catheter. The objective of this prior system is to provide frictional engagement to not only form a fluid-tight seal but also to secure the occlusion device to the deployment catheter until the desired deployment of the occlusion device. When fluid is applied within the lumen of the deployment catheter, the distal end portion of the deployment catheter expands outwardly and the proximal end portion of the occlusion device is release, thereby deploying the occlusion device.

There remains a need for a coupling assembly that provides a high strength attachment between the occlusion device and the deployment catheter during the advancement of the occlusion device through the vasculature of a patient, and also allows for a rapid release of the occlusion device at the desired time of deployment, without having to rely upon tight sizing relationships between tubular members and tubular expansion.

SUMMARY OF INVENTION

The present invention embodies occlusion devices for use with hydraulic deployment systems. The occlusion devices include a headpiece that can be inserted into a distal end portion of a lumen of a hydraulic deployment system deployment catheter. A deformable interference element, which has an initial configuration and a deformed configuration, is located at the proximal end portion of the headpiece. In the initial configuration, the interference element engages a section of the distal end portion of the deployment catheter to secure the headpiece within the lumen and to provide a high strength attachment between the occlusion device and the deployment catheter. When sufficient fluid pressure is applied to the interference element, the pressure causes the interference element to transition into the deformed configuration. In the deformed configuration, the engagement between the interference element and the distal end portion of the deployment catheter lessens, or the interference element completely disengages from the distal end portion of the deployment catheter, and the headpiece is allowed to be advanced out of the lumen of the deployment catheter.

In one preferred embodiment, the distal end of the deployment catheter is comprised of a substantially rigid sleeve, such as a metal hypotube. The proximal end portion of the sleeve includes a ridge or lip that provides an interference surface. An occlusion device having a cylindrical headpiece is inserted into the sleeve. The proximal end portion of the headpiece has an interference element in the form of a radial flare that extends radially from the proximal end portion of the headpiece. The radial flare has a diameter larger than that of the proximal end portion of the sleeve and engages the lip at the proximal end portion of the sleeve to secure the headpiece within the sleeve.

In another preferred embodiment, the headpiece can include a relief area that accommodates the deformation of the deformable interference element. The relief area can comprise a space which allows a portion(s) of the headpiece to flex or bend to aid in the deformation of the interference element.

When it is desired to deploy the occlusion device, fluid is introduced into the lumen of the deployment catheter to apply fluid pressure to the interference element. The fluid pressure causes the radial flare to slightly fold or deform so the flare is allowed to be pushed distally past the lip of the sleeve and the headpiece is allowed to be pushed out of the distal end of the sleeve.

Other aspects, objects and advantages of the present invention will be understood from the following description according to the preferred embodiments of the present invention, specifically including stated and unstated combinations of the various features which are described herein, relevant information concerning which is shown in the accompanying drawings.

BRIEF DESCRIPTION OF THE DRAWINGS

In describing the preferred embodiments of the present invention, reference will be made to the accompanying drawings, wherein:

FIG. 1 is an enlarged partially sectioned view of an occlusion device deployment system in accordance with a preferred embodiment of the present invention;

FIG. 2 is an enlarged partially sectioned view of the occlusion device deployment system shown in FIG. 1, during release of the occlusion device;

FIG. 7 is an enlarged partially sectioned view of one embodiment of an occlusion device deployment system in combination with another embodiment of the occlusion device;

FIG. 8 is an enlarged partially sectioned view of the occlusion device deployment system shown in FIG. 7, during release of the occlusion device;

FIG. 9 is a cross-sectional view of another embodiment the coupling element in accordance with the present invention, shown after the coupling element has been deformed; and FIG. 10 is a cross-sectional view of the coupling element of FIG. 9 shown connected to a headpiece having a tubular configuration.

DESCRIPTION OF THE PREFERRED EMBODIMENTS

Figure 3:
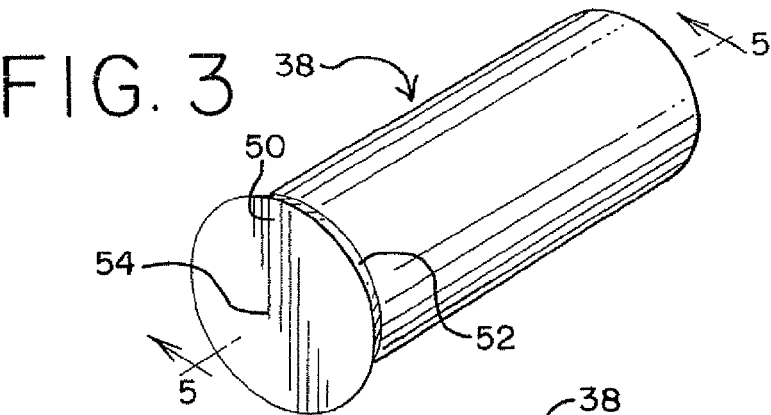
FIG. 3 is a perspective view of one embodiment of a coupling element in accordance with the present invention, shown prior to deformation of the interference element.

As required, detailed embodiments of the present invention are disclosed herein; however, it is to be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

FIGS. 1 and 2 generally illustrate a preferred embodiment of the hydraulic occlusion device deployment system and occlusion device of the present invention. The deployment system, generally designated at 10, includes an elongated deployment catheter 12 that can be inserted and advanced through a guide catheter (not shown) to guide an occlusion device 11 to a preselected site within the vascular 14 of a patient in a manner generally known in the art.

The illustrated deployment catheter 12 is comprised of a series of ribbon coils 16 enclosed within a polymer sheath 18. It will be understood that the deployment catheter can be any type of deployment catheter suitable for deployment of occlusion devices. The deployment catheter 12 includes a proximal end portion (not shown) and a distal end portion 20. A lumen 22 extends along the deployment catheter 12 from the proximal end portion to the distal end portion 20.

A hydraulic source (not shown) is operatively connected to the proximal end portion of the deployment catheter 12 to inject fluid into the deployment catheter lumen 22 and to increase fluid pressure within said lumen. The hydraulic source can be similar to the hydraulic syringe system disclosed in U.S. Pat. No. 6,544,225 to Lulo, et al., assigned to the same assignee of the present application and incorporated herein by reference. The hydraulic source could also be any other suitable hydraulic source known in the art. Typical hydraulic fluid is saline solution or other material suitable for internal medical use.

A coupling sleeve 24 is located at the distal end portion 20 of the deployment catheter 12. The coupling sleeve 24 has a tubular configuration that includes a lumen 26 (shown in FIG. 2) which communicates with lumen 22. The coupling sleeve 24 is preferably made of a rigid or semi-rigid material so that the configuration of the coupling sleeve does not substantially change, i.e., expand, upon an increase in fluid pressure within the lumen 26. Preferably, the coupling sleeve is comprised of a metal hypotube. Alternatively, the coupling sleeve 24 can be comprised of any other rigid or semi-rigid material that does not change configuration in response to fluid pressure within a catheter, such as a high Durometer polymer.

The coupling sleeve 24 has an indented proximal end portion 28 that is sized to fit into the lumen 22 at the distal end portion 20 of deployment catheter 12. The coupling sleeve 24 and the deployment catheter 12 are preferably separate components that are secured together by, for example, adhesive or solder. It is also contemplated that the coupling sleeve 24 and the deployment catheter 12 could be a unitary structure form by, for example, extrusion or molding.

The occlusion device 11 includes an embolic element 30 and a headpiece 32 which are illustrated as separate components that are secured together by adhesive or solder; however, it will be understood that the embolic element 30 and the headpiece 32 can be of a unitary structure which forms the occlusion device.

The embolic element 30 is preferably an embolic coil which can be of the type that takes a substantially linear configuration for being advanced through the guide catheter and a randomly oriented relaxed condition after it has exited from the guide catheter. Alternatively, the embolic element 30 may be any other type of embolic element which may take on various forms and configurations, such as hydrogels, foams, bioactive coils, braids, cables and hybrid devices.

The occlusion device headpiece 32 has a distal end portion 34 and an indented proximal end portion 36. The distal end portion 34 is connected to the embolic element 30, and the proximal end portion 36 is sized to fit within the lumen 26 of the coupling sleeve 24.

A coupling element 38 is located at the proximal end portion 36 of the headpiece 32. In the illustrated embodiment, referring to FIGS. 5 and 6, the coupling element 38 is generally cylindrical and includes a proximal wall 40 and a circumferential sidewall 42 defining a cavity 44 within the coupling element. An opening 46 is located at the distal end 48 of the coupling element 38. The coupling element 38 is attached to the headpiece 32 by placing the coupling element over the indented proximal end portion 36 of the headpiece so that the proximal end portion 36 of the headpiece enters the opening 46 and is located within the cavity 44 of the coupling element, as shown in FIGS. 1 and 2. The coupling element 38 and the headpiece 32 are then secured together, for example, by adhesives or solder. The proximal end portion 36 of the headpiece 32 is indented so that the circumferential sidewall 42 of the coupling element 38 can fit between the headpiece 32 and the coupling sleeve 24. When desired, the size of the indent of the proximal end portion 36 of the headpiece 32 is substantially equal to the thickness of the circumferential sidewall 42 so that the outer surface of the circumferential wall and outer surface of the headpiece generally align.

Figure 4:
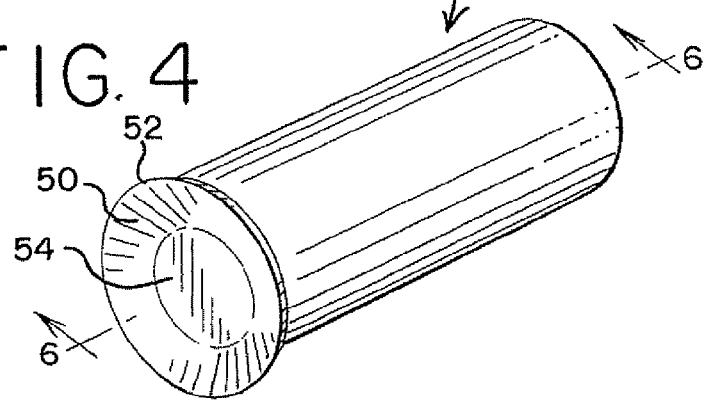
FIG. 4 is a perspective view of the coupling element of FIG. 3, shown after the interference element has been deformed.
Figure 5:
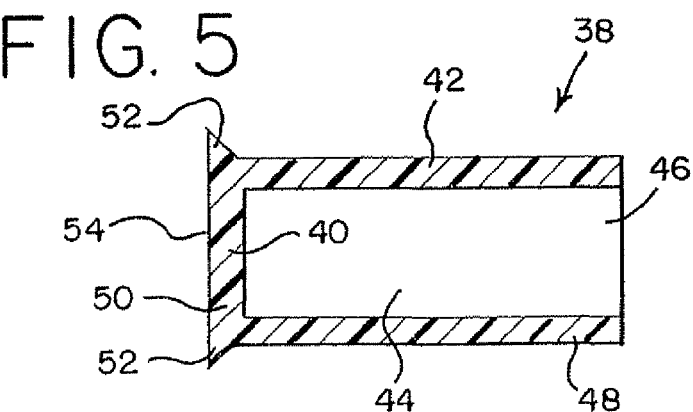
FIG. 5 is a cross-sectional view of the coupling element shown in FIG. 3, taken along lines 5-5.
Figure 6:
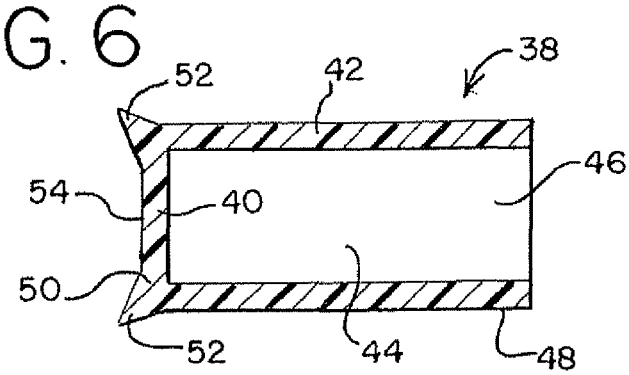
FIG. 6 is a cross-sectional view of the coupling element shown in FIG. 4, taken along lines 6-6.

Referring to FIGS. 3, 4, 5 and 6, the proximal wall 40 of the coupling element 38 includes a deformable interference element 50. Illustratively, the deformable interference element 50 is comprised of a radially flared proximal tip 52 of the coupling element. The deformable interference element 50 includes an initial configuration, as illustrated in FIGS. 3 and 5, and a slightly deformed or folded configuration, as illustrated in FIGS. 4 and 6. Preferably, the interference element 50 is made from a deformable material that will deform when a hydraulic pressure between about 100 psi and about 1000 psi, typically between about 200 psi and about 900 psi, is applied to the interference element. Such materials include flexible metals, metal alloys, such as Nitinol, and deformable polymers.

Referring to FIGS. 3 and 5, in the initial configuration, the flared proximal tip 52 is flared radially and the outer surface 54 of the proximal wall 40 is flat. When the headpiece 32 is placed within the coupling sleeve 24 prior to deployment, the radial flared proximal tip 52 engages an interference surface located on the deployment catheter. In the illustrated embodiment, the radial flared proximal tip 52 has a larger diameter then a lip 56 located at the proximal end of the coupling sleeve 24, and the radial flared proximal tip 52 engages with the lip 56 to provide a high strength attachment between the headpiece 32 and the coupling sleeve 24, as illustrated and FIG. 1.

Referring to FIG. 2, when fluid 58 enters the lumen 22 and hydraulic pressure is applied to the coupling element 38, the interference element 50 transitions into a deformed configuration. In the deformed configuration, the flared proximal tip 52 is slighted folded or deformed inwardly. In the illustrated embodiments, the surface 54 of the proximal wall 40 of the coupling element 38 is thereby curved in a concaved dish-like shape, as illustrated in FIGS. 2, 4 and 6. The deformed configuration allows the flared proximal tip 52 of the coupling member 38 to be advanced distally past the lip 56 of the coupling sleeve 24, and the headpiece 32 is pushed out to the lumen 26 of coupling sleeve 24 under the force of the hydraulic pressure.

In use, with the flared proximal tip 52 of the coupling member 38 in the initial configuration and engaging lip 56 of the coupling sleeve 24, the headpiece 32 of the occlusion device 11 is disposed within the lumen 26 of the coupling sleeve 24 to securely attach the occlusion device 11 to the deployment catheter 12, as illustrate in FIG. 1.

A guide catheter can be inserted into the vasculature system of a patient, and the distal end portion of the guide catheter can be positioned at a preselected location within a blood vessel, typically in conjunction with other devices and professional procedures as generally known in the art. The deployment catheter 12 having an occlusion device 11 is inserted into a proximal end portion of the guide catheter, and the deployment catheter 12 is advanced through the guide catheter until the occlusion device 11 reaches the distal end portion of the guide catheter.

Once the occlusion device 11 reaches the distal end portion of the guide catheter, the occlusion device 11 may be moved out of the distal end portion of the guide catheter by moving the guide catheter in a retrograde manner, by advancing the deployment catheter 12, or by a combination of moving the guide catheter in a retrograde manner and advancing the deployment catheter.

The occlusion device 11 can include at least one radiopaque marker, preferably located in the headpiece 32, so that the position of the occlusion device 11 can be monitored by fluoroscopy. After the occlusion device 11 has exited the guide catheter, if it is determined that the occlusion device is in the wrong position and/or a different occlusion device is required, the deployment catheter 12 can be retracted to move the occlusion device back into the guide catheter. Once in the guide catheter, the occlusion device 11 can be repositioned or completely removed from the patient.

After it has been determined that the occlusion device 11 is at the desired location within the patient, the hydraulic source is activated to inject fluid 58 into the lumen 22 of the deployment catheter 12 and to increase the fluid pressure within the lumen 22. The increased fluid pressure is applied to the coupling element 38 which causes the interference element 50 to deform, e.g., the flared proximal tip 52 slightly folds or deforms inward, as illustrated in FIG. 2. With the interference element 50 deformed, hydraulic pressure advances the interference element 50 past the lip 56 of the coupling sleeve 24, and the headpiece 32 is pushed out of the coupling sleeve 24, thereby deploying the occlusion device.

FIGS. 7 and 8 illustrate the deployment system 10 that is illustrated in combination with an alternative embodiment of the occlusion device, generally designated as 11a.

In the alternative embodiment of the occlusion device 11a, the proximal end portion 36a of the headpiece 32a of the occlusion device at least partially defines a relief area 37a (FIG. 7) that allows the proximal wall 40a of the coupling element 38a to deform, typically be flexing or bending, which aids in the deformation of the interference element 50a (FIGS. 8 and 9). For example, to release the occlusion device 11a from the delivery catheter 12, wall 40a bends in an arcuate manner so that proximal end surface 54a has a concave-like shape which draws the flared tip 52a of the interference element 50a radially inward so that the interference element disengages lip 56.

The relief area 37a is a space that accommodates the deformation of coupling element 38a by receiving a portion of the coupling element. Preferably, the relief area 37a can be at least partially defined by the proximal end portion 36a of the headpiece 32a. In the embodiment illustrated in FIGS. 7 and 8, the relief area 37a is defined by a concave proximal end surface 41a. The relief area 37a defined by the concave surface receives a portion of wall 40a allowing the wall to bend, thereby deforming the flared tip 52a by drawing the flared tip radially inward.

As illustrated in FIG. 10, in an alternative embodiment, the headpiece could have a proximal end portion 36b that is open ended, such as being of a tubular shape. With this approach, the opening in the lumen 43b of the tubular proximal end portion 36b of the headpiece defines a relief area 37b.

The operation of the deployment system of FIGS. 7 and 8 is similar to the operation of the deployment system illustrated in FIGS. 1 and 2. The deployment catheter 12 is manipulated to guide and position the occlusion device 11a at a desired delivery site within the body. Once the occlusion device 11a is at the desire location, the hydraulic source is activated to increase the fluid pressure within lumen 22. The increased fluid pressure acts upon wall 40a of coupling element 38a causing wall 40a to bend (FIGS. 8 and 9). When wall 40a bends, a portion of the wall moves into and occupies the relief space 37a, and the flared proximal tip 52a of interference element 50a is drawn radially inward, thereby disengaging the flared tip 52a from lip 56. With the flared tip 52a drawn radially inward, hydraulic pressure advances the interference element 50a past lip 56 of the coupling sleeve 24, and the headpiece is pushed out of the coupling sleeve to deploy the occlusion device 11a.

It will be understood that the embodiments of the present invention which have been described are illustrative of some of the applications of the principles of the present invention. Numerous modifications may be made by those skilled in the art without departing from the true spirit and scope of the invention, including those combinations of features that are individually disclosed or claimed herein.

The invention claimed is:

1. An occlusion device for use with a hydraulic deployment system, comprising:
    an occlusion device having a proximal end portion, said proximal end portion sized for insertion into a lumen of a deployment catheter of a hydraulic deployment system;
    a deformable interference element located on the proximal end portion of the occlusion device, said deformable interference element having an initial configuration and a deformed configuration;
    said deformable interference element comprises a body with an outer surface of a diameter and a deformable radial flare extending radially outward beyond said body outer surface diameter, said deformable radial flare having an initial configuration and a deformed condition;
    said deformable interference element radial flare in its initial configuration engages a lip that is a radially inwardly extending inner surface of a radially inwardly indented distal portion of the deployment catheter, the radially inwardly indented portion having an inner diameter greater than the diameter of the body outer surface of the deformable interference element and less than said deformable radial flare in its initial configuration;
    wherein the radial flare secures the proximal end portion of the occlusion device to the deployment catheter when the radial flare is in the initial configuration; and
    wherein the proximal end portion of the occlusion device is removable from the deployment catheter when the radial flare is in the deformed condition and disengages the lip.

2. The occlusion device of claim 1 in which the proximal end portion of the occlusion device comprises an occlusion device headpiece having a surface defining a relief area.

3. The occlusion device of claim 2 in which the proximal end portion of the occlusion device comprises a headpiece that is open ended at its proximal end, and the relief area is defined by an opening at said proximal end of the headpiece.

4. The occlusion device of claim 1 in which the proximal end portion of the occlusion device is cylindrical.

5. The occlusion device of claim 1 in which the interference element is comprised of a flexible polymer.

6. The occlusion device of claim 1 in which the interference element transitions from the initial configuration to the deformed configuration when hydraulic pressure is applied to the interference element.

7. The occlusion device of claim 6 in which said transition takes place when the hydraulic pressure is 100 psi or greater.

8. The occlusion device of claim 1 in which the occlusion device includes an embolic coil.

9. An occlusion device comprising:
    an occlusion device having a proximal end portion, said proximal end portion of the occlusion device removably disposed within a lumen of a deployment catheter;
    a deformable interference element located on the proximal end portion of the occlusion device, said deformable interference element transitioning from an initial configuration to a deformed configuration upon an increase in hydraulic pressure within the lumen of the deployment catheter;
    said occlusion device including a relief area that accommodates the deformation of the deformable interference element;
    wherein the deformable interference element engages an interference surface on the deployment catheter to secure the proximal end portion of the occlusion device in the lumen of the deployment catheter when the deformable interference element is in the initial configuration;
    wherein the deformable interference element disengages the interference surface on the deployment catheter when the interference element is in the deformed configuration, allowing the proximal end portion of the occlusion device to be removed from the lumen of the deployment catheter; and
    the proximal end portion of the occlusion device comprises an occlusion device headpiece having a concave surface defining the relief area.

10. The occlusion device of claim 9 in which the proximal end portion of the occlusion device is cylindrical and the interference element comprises a deformable radial flare extending from the proximal end portion of the occlusion device.

11. The occlusion device of claim 9 in which the interference element is comprised of a flexible polymer.

12. The occlusion device of claim 9 in which the interference element transitions from the initial configuration to the deformed configuration when hydraulic pressure is applied to the interference element.

13. The occlusion device of claim 9 in which said transition takes place when the hydraulic pressure is 100 psi or greater.

14. The occlusion device of claim 9 in which the occlusion device includes an embolic coil.

15. The occlusion device of claim 9, wherein the occlusion device headpiece is open-ended at a proximal end, and the relief area is defined by an opening at said proximal end of the headpiece.

* * * * *